United States Patent [19]

Halm et al.

[11] Patent Number: 4,829,548
[45] Date of Patent: May 9, 1989

[54] DENTAL X-RAY EXAMINATION APPARATUS

[75] Inventors: Jan H. Halm, Hilversum; Leonardus H. J. Post; Johannes F. van Otterdijk, both of Eindhoven; Paul F. van der Stelt, Amstelveen, all of Netherlands

[73] Assignee: U.S. Philips Corporation, New York, N.Y.

[21] Appl. No.: 621,412

[22] Filed: Jun. 18, 1984

[30] Foreign Application Priority Data

Jun. 23, 1983 [NL] Netherlands ............ 8302233

[51] Int. Cl.⁴ ............................................. G03B 42/02
[52] U.S. Cl. ....................................... 378/38; 378/189; 378/191
[58] Field of Search .................. 378/189, 38, 191, 170

[56] References Cited

U.S. PATENT DOCUMENTS

| | | | |
|---|---|---|---|
| 4,012,638 | 3/1977 | Alschuler et al. | 378/170 |
| 4,057,733 | 11/1977 | Hofmouzel et al. | 378/170 |
| 4,409,616 | 10/1983 | Ledley | 378/99 |
| 4,426,716 | 1/1984 | Muether et al. | 378/197 |

FOREIGN PATENT DOCUMENTS 1538561 of 1979 United Kingdom.

OTHER PUBLICATIONS van Aken, J., "Optimum Conditions for Intraoral Roentgenograms", *Oral Surgery, and Oral Pathology*, vol. 27, No. 4, pp. 475–491 (Apr. 1969).

*Primary Examiner*—Carolyn E. Fields
*Attorney, Agent, or Firm*—Thomas A. Briody; Jack E. Haken; Jack D. Slobod

[57] ABSTRACT

An X-ray examination apparatus, for example, for dental use, comprises an extraoral radiation entrance screen which is displaceable in a plane which is transverse with respect to a normal thereto. Consequently, distortion-free imaging can be performed for the entire set of teeth and the adjoining regions of the jaws.

5 Claims, 1 Drawing Sheet

DENTAL X-RAY EXAMINATION APPARATUS

BACKGROUND OF THE INVENTION

The invention relates to an X-ray examination apparatus. The apparatus comprises an X-ray tube provided with an anode pipe. The anode pipe accommodates, at an end thereof remote from the tube, an anode and a radiation window, and an X-ray detection device.

An X-ray examination apparatus of this kind is described in U.S. Pat. No. 4,057,733. The dental apparatus described therein comprises an X-ray source with an anode pipe. The anode pipe can be inserted into the mouth of the patient for the formation of images, so that the X-ray focus and hence the source are intraoral. For X-ray fluoroscopy, the apparatus further comprises an extraoral radiation detection device which is an X-ray image intensifier tube. The X-ray image intensifier tube is arranged so as to be displaceable along the direction of a principal ray of the image forming X-ray beam and rotatable about the X-ray tube.

During the process of scanning a set of teeth by means of such an apparatus, freedom of movement is restricted. Moreover, because the radiation is incident at different angles for different members of a set of teeth, distortion occurs, and a change over of the scanning process from that for the upper set of teeth to that for the lower set of teeth and vice versa is comparatively difficult. Moreover, the introduction of such a range of movement also reduces the degree of reliability with respect to correct image formation.

SUMMARY OF THE INVENTION

It is an object of the invention to mitigate these drawbacks. According to the invention an X-ray examination apparatus is provided with means for displacing the entrance screen of the X-ray detection device in two directions in a plane which is transverse with respect to a normal to the entrance screen.

Because the radiation entrance screen in an X-ray examination apparatus according to the invention is displaceable in a plane which is transverse with respect to the normal to the entrance screen, by using parallel techniques, for example as described in the article by J. van Aken entitled "Optimum conditions for intraoral roentgenograms" (*Oral Surgery, Oral Medicine & Oral Pathology*, Vol. 27, No. 4, pages 475–491, April 1969), all the members of a set of teeth can be imaged without distortion. At the same time, the position of the detector does not have an undesirable amount of freedom of movement.

In a preferred embodiment, the two lateral displacements of the detector are performed by means of, for example, screw threaded spindle drives. If necessary, each drive may also include a level gear for accommodating an angle between a control spindle direction and the displacement direction. The control spindles are preferably provided with manually operable knobs. For a suitably reproducible setting, the apparatus may be provided with marks which are related to the displacements.

The radiation entrance screen in a preferred embodiment is the entrance screen of, for example a 5 cm X-ray image intensifier tube. Such a tube produced a comparatively high degree of brightness intensification thus allowing a comparatively low radiation dose to be used for making radiographs as well as for fluoroscopy.

The entrance screen of the intensifier tube preferably contains CsI as the entrance phosphor. The phosphor layer may be provided on the outer surface of an entrance window. The photocathode of the intensifier tube is then provided opposite the entrance phosphor on the inner surface of the window. Image scatter can be prevented by using a fiber optic plate for the entrance window.

The image formed on the exit window of the X-ray image intensifier tube can be read, for example, by a television camera tube which is coupled thereto. However, a direct picture of the exit image can also be made, for example, by an instant print camera.

On the other hand, a matrix of semiconductor radiation detectors may be provided on the exit screen, or the exit screen itself may comprise a matrix of electron-sensitive semiconductor detector elements.

Alternatively, the X-ray image can itself be directly picked up by a television camera tube provided with an X-ray-sensitive entrance screen which then forms the entrance screen of the detection device. Such a camera tube may contain, for example, selenium as the radiation sensitive material. For recording an image for analysis, a preferred embodiment includes a video memory and a television monitor. This embodiment may also include a V.H.U. (Video Hard copy Unit) for making hard copies.

Because the entrance screen, and hence the imaging plane, is always oriented parallel to the object plane in the apparatus according to the invention, as has already been stated, there is no geometrical distortion in the image. The main ray of the X-ray beam in principle extends transverse with respect to the tangent to the dental arch in the image. The half-shadow occurring in the image can be reduced by utilizing an X-ray tube in which a small focal spot is formed on the anode as the generating point for radiation. The cross-section of the X-ray beam can be adapted to the transverse dimension and the position of the entrance screen by a diaphragm.

DESCRIPTION OF THE PREFERRED EMBODIMENTS

Figure 1:
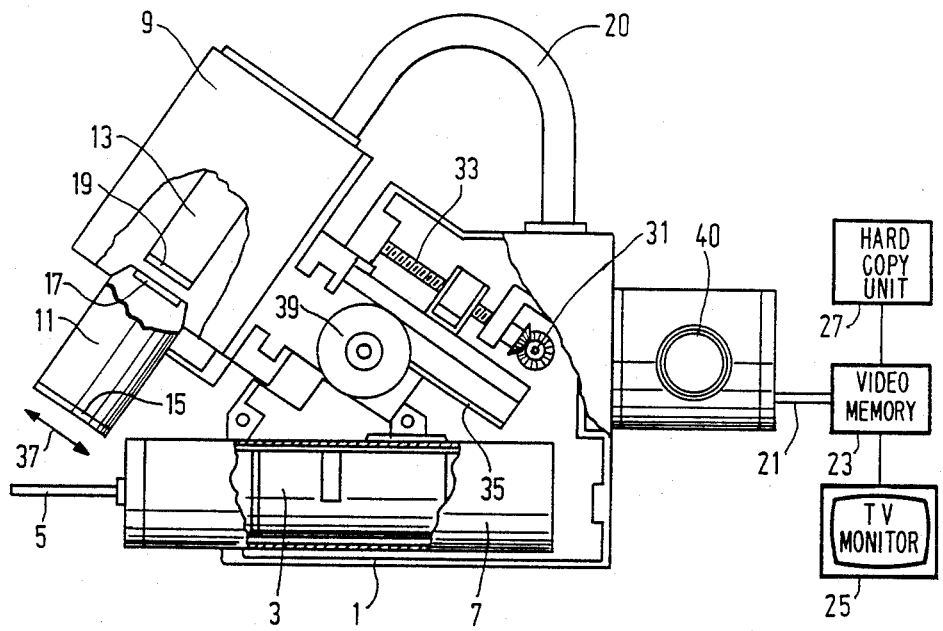
FIG. 1 shows an X-ray examination apparatus according to the invention.

Referring to FIG. 1, the X-ray examination apparatus according to the invention comprises a first housing 1. Housing 1 accommodates an X-ray tube 3 with a hollow anode pipe 5 and a high voltage generator 7. The examination apparatus further includes a second housing 9 which in this case accommodates an X-ray image intensifier 11 and a television camera tube 13. The X-ray image intensifier tube 11 comprises an entrance screen 15 with a phosphor screen and a photocathode, and an X-ray image exit screen 17 with, for example, again a phosphor screen. An entrance window 19 of the television camera tube is optically coupled to the exit window 17 of the X-ray image intensifier tube 11, for example, by a lens system or a fiber optical plate (not shown). The exit window 17 may also consist of a fiber optical plate.

Via a signal lead 21, video signals generated by the television camera tube 13 are applied, via a video memory 23, to a television monitor 25 and, if desired, to a hard copy unit 27.

Using a knob 31 and a spindle 33, the second housing 9 can be displaced along a guide 35 with respect to the first housing 1 in a direction in the plane of the drawing which is indicated by an arrow 37. Via a further spindle which is operated by an external knob 39. The second housing 9 can be displaced in a direction which is transverse with respect to the plane of drawing, the entrance screen 15 of the X-ray image intensifier tube 11 then moves, as during the previous displacement, in a plane which is transverse with respect to the normal to the entrance screen 15.

Instead of an X-ray image intensifier tube, an X-ray sensitive screen can be used to record the X-ray image. The screen can be used to record the image either directly or via an intermediate X-ray intensifier screen.

In order to take optimum advantage of the distortion-free imaging process, the entrance screen of the detection device is preferably flat. For example, for a 5 cm X-ray image intensifier tube it is quite satisfactory to use a flat entrance screen. If desired, the facility for image reduction provided by the X-ray image intensifier tube need not be employed enabling a 5 cm exit screen to be used. An adapted entrance screen of a camera tube may be coupled to such an exit screen or the exit screen can be projected in reduced form onto the entrance screen of the camera tube by optical means.

An advantageous embodiment of the invention utilizes a so-called SIT image intensifier tube as described in British Pat. No. 1,538,561. Such an X-ray image intensifier tube includes an exit screen in which the electron image is directly converted, via a mosaic of semiconductor detection elements, into an image signal which can be read electronically.

For image storage for prolonged periods of time, a digital image memory may be connected to the apparatus, for example via an analog-to-digital converter.

Also shown is a cable housing 38 to which a bushing 40 is secured. By means of bushing 40, the apparatus can preferably be suspended so as to be translatable and rotatable from a ceiling support.

What is claimed is:

1. An X-ray examination apparatus comprising:
   an X-ray tube having an anode pipe;
   an X-ray detection device having an entrance screen; and
   means for displaceably connecting the X-ray tube and the X-ray detection device so that the entrance screen of the X-ray detection device can be displaced relative to the X-ray tube in two directions in a plane which is transverse to a normal to the entrance screen;
   characterized in that the means for displaceably connecting the X-ray tube and the X-ray detection device comprises first and second screw threaded spindle drives, the first spindle drive displacing the entrance screen in a first direction and the second spindle drive displacing the entrance screen in a second direction perpendicular to the first direction.

2. An X-ray examination apparatus as claimed in claim 1, characterized in that the detection device comprises an image intensifier tube having a flat entrance screen.

3. An X-ray examination apparatus as claimed in claim 1, characterized in that the detection device comprises an X-ray luminescent screen and a device for recording optical images generated in the screen.

4. An X-ray examination apparatus as claimed in claim 1, characterized in that the detection device comprises an X-ray image intensifier tube having an exit screen comprising a mosaic of electron sensitive semiconductor detection elements.

5. An X-ray examination apparatus as claimed in claim 1, characterized in that the detection device comprises an instant camera.

* * * * *